United States Patent [19]
Wise

[11] Patent Number: 5,968,204
[45] Date of Patent: Oct. 19, 1999

[54] ARTICLE FOR CLEANING SURFACES

[75] Inventor: Rodney Mahlon Wise, Wyoming, Ohio

[73] Assignee: The Procter & Gamble Company, Cincinnati, Ohio

[21] Appl. No.: 09/117,819

[22] PCT Filed: Feb. 6, 1997

[86] PCT No.: PCT/US97/01661

§ 371 Date: Aug. 7, 1998

§ 102(e) Date: Aug. 7, 1998

[87] PCT Pub. No.: WO97/29178

PCT Pub. Date: Aug. 14, 1997

Related U.S. Application Data

[60] Provisional application No. 60/011,447, Feb. 9, 1996.

[51] Int. Cl.$^6$ .............................. C11D 17/04; C11D 3/20; A47L 13/17; A47L 25/08
[52] U.S. Cl. ................................. 8/142; 8/137; 510/277; 510/281; 510/282; 510/283; 510/284; 510/285; 510/289; 510/291; 510/293; 510/294; 510/295; 510/297; 510/108; 510/109; 510/119; 510/160; 510/275; 510/278; 510/280; 442/110; 442/115; 442/164; 442/168; 142/171; 428/365; 428/397
[58] Field of Search ........................ 8/142, 137; 510/277, 510/281, 282, 283, 284, 285, 289, 291, 293, 294, 295, 297, 108, 109, 119, 160, 275, 278, 280; 442/110, 115, 164, 168, 171; 428/365, 397

[56] References Cited

U.S. PATENT DOCUMENTS

| | | |
|---|---|---|
| 4,336,024 | 6/1982 | Denissenko et al. .................. 8/142 |
| 4,551,143 | 11/1985 | Cook et al. ............................. 604/371 |
| 4,630,312 | 12/1986 | Milstein . | 
| 4,943,392 | 7/1990 | Hastedt et al. . |
| 5,009,747 | 4/1991 | Viazmensky et al. . |
| 5,062,973 | 11/1991 | Kellett . |
| 5,066,413 | 11/1991 | Kellett . |
| 5,080,822 | 1/1992 | Van Eenam . |
| 5,173,200 | 12/1992 | Kellett . |
| 5,238,587 | 8/1993 | Smith et al. . |
| 5,292,581 | 3/1994 | Viazmensky et al. . |
| 5,492,540 | 2/1996 | Leifheit et al. ........................ 8/111 |
| 5,547,476 | 8/1996 | Siklosi et al. ......................... 8/142 |
| 5,591,236 | 1/1997 | Roetker ................................. 8/137 |
| 5,630,847 | 5/1997 | Roetker ................................. 8/137 |
| 5,630,848 | 5/1997 | Young et al. ......................... 8/137 |
| 5,632,780 | 5/1997 | Siklosi .................................. 8/137 |
| 5,658,651 | 8/1997 | Smith et al. . |
| 5,681,355 | 10/1997 | Davis et al. .......................... 8/137 |
| 5,687,591 | 11/1997 | Siklosi et al. . |
| 5,746,776 | 5/1998 | Smith et al. .......................... 8/142 |
| 5,762,648 | 6/1998 | Yeazell ................................. 8/137 |
| 5,789,368 | 8/1998 | You et al. ............................. 510/297 |

FOREIGN PATENT DOCUMENTS

| | | |
|---|---|---|
| 0 344 847 A2 | 5/1989 | European Pat. Off. . |
| 0 429 172 A1 | 10/1990 | European Pat. Off. . |
| WO 90/05771 | 5/1990 | WIPO . |
| WO 96/30471 | 10/1996 | WIPO . |
| WO 96/30580 | 10/1996 | WIPO . |
| WO 96/37652 | 11/1996 | WIPO . |

*Primary Examiner*—Alan Diamond
*Attorney, Agent, or Firm*—Steven R. Chuey; Kim W. Zerby; Jacobus C. Rasser

[57] ABSTRACT

Sheets capable of developing a positive electostatic charge are used for a variety of surface cleaning operations. Polyester fabric, non-woven and chemically bonded with an acrylic latex is used to dust surfaces, to clean clothes, furniture and carpets. A light solvent such as isopropanol can be used with the sheets to loosen gummy soils. In one mode, the sheets are used in a hot air clothes dryer to remove soils and detritus from garments. Processes for cleaning a variety of fabric and hard surfaces are conducted using the sheets.

26 Claims, 3 Drawing Sheets

ARTICLE FOR CLEANING SURFACES

CROSS REFERENCE

This application is a 371 of PCT application Ser. No. PCT/US97/01661, filed on Feb. 6, 1997, which claims the benefit under 35 U.S.C. § 119(e) of U.S. Provisional Application Ser. No. 60/011,447, filed on Feb. 9, 1996.

FIELD OF THE INVENTION

The present invention relates to cleaning cloths for dry wipe cleaning of household surfaces such as carpets, upholstery and clothing. The cloths can also be used to clean environmental surfaces such as furniture, floors, and the like, in an improved dusting operation.

BACKGROUND OF THE INVENTION

Household cleaning tasks are conducted using articles and compositions which are designed to remove dirt and residues from a wide variety of surfaces. For example, items such as simple dust cloths and mops are conventionally used to remove particulate matter from hard surfaces such as furniture. Such items are often supplemented by spray-on waxy or oily compositions which are designed to enhance the uptake of dirt particles. Fabric surfaces are conventionally cleaned using various surfactants and surfactant pastes. For example carpet and furniture fabrics are typically scrubbed and/or cleaned by means of surfactants and/or solvents which are designed to loosen oily dirt from the fabrics, and the resulting residues are sometimes absorbed into a material such as clay or kieselguhr, which is then discarded. Garments and other fabrics such as draperies, tablecloths, and the like, are often cleaned by immersion processes involving various organic solvents and/or by conventional wet processes involving detersive surfactants and water, either in an immersion or spray-on operation.

In many instances, surface cleaning operations involve the application of small quantities of "pre-spotting" agents to discrete, highly stained areas of the article being cleaned. While effective for their intended use, such localized spot removal treatment compositions are generally expensive on a per-use basis and would not be suitable for large scale cleaning operations.

Accordingly, there is a continuing search for simple, effective cleaning processes and compositions for use by the consumer. Moreover, there is a continuing search for approved cleaning compositions which are cost effective.

The present invention provides a cleaning cloth for what can be termed "dry-wipe" cleaning of household surfaces such as carpets, upholstery, clothing, and the like. The dry-wipe cleaning articles herein can be passed across such surfaces, and oils, particulates and gummy residues are transferred onto the wipe fabric. The practice of the invention provides an unexpectedly high level of cleaning, approaching wet detergent cleaning in some cases, but without the mess, prospective damage and resoiling potential occasioned by the presence of unremoved wet detergent residues. In another mode, the articles and processes herein can be used in a conventional "dusting" operation on hard, non-fabric surfaces. In yet another mode, the articles herein can be used to clean living beings, e.g., the hair on domestic pets, farm animals, as well as to clean human hair and skin.

SUMMARY OF THE INVENTION

The present invention encompasses an article, typically a fibrous article, for cleaning surfaces, comprising:

(a) a substrate, said substrate being characterized by its oleophilic nature and its ability to acquire a strong electrostatically positive charge when passed across the surface being cleaned; and (b) said substrate releasably containing an auxiliary cleaning composition, preferably a monohydric alcohol which is a member selected from the group consisting of ethanol, isopropanol, and mixtures thereof.

A preferred article herein is wherein the substrate comprises polyester fibers. An especially preferred article is wherein the substrate is SOMMERS STYLES 235 and 265.

In one embodiment, the auxiliary cleaning composition can comprise a member selected from the group consisting of methoxy-, ethoxy-, propoxy- and butoxy-propoxypropanol. In another embodiment, the auxiliary cleaning composition comprises 1,2-octanediol. In yet another embodiment, the auxiliary cleaning composition can comprise a nonionic surfactant. The auxiliary cleaning composition can comprise mixed ingredients, such as a mixture of butoxy-propoxypropanol and 1,2-octanediol, and a mixture of butoxy-propoxypropanol, 1,2-octanediol and an ethoxylated alcohol or alkyl phenol.

In an optional mode, the article herein is designed for use in a hot air clothes dryer. Under such circumstances, the article can comprise an aqueous cleaning/refreshment composition. Such compositions will typically comprise water (up to about 99.95%, by weight) and from about 0.05% to about 2.5%, by weight, of a nonionic surfactant, especially an ethoxylated $C_{12}$–$C_{18}$ alcohol.

The invention also encompasses a process for cleaning fabrics in a conventional automatic clothes dryer, comprising the steps of placing soiled fabrics together with the substrates herein, especially in sheet form, or with an article according to any of the foregoing embodiments, in the drum of the clothes dryer, and operating the dryer under conventional usage conditions involving rotation of the dryer drum and the introduction of hot air into the drum.

All percentages, ratios and proportions herein are by weight, unless otherwise specified. All documents cited are, in relevant part, incorporated herein by reference.

DETAILED DESCRIPTION OF THE INVENTION

Figure 1:
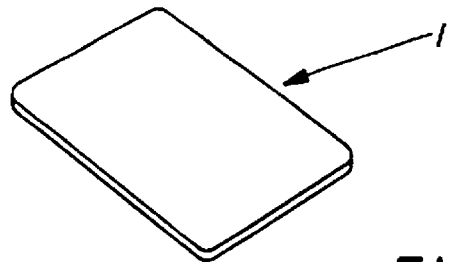
FIG. 1 is a sheet of the present type (1) for placement in the containment bag which is used in the in-dryer mode of the present process.
Figure 2:
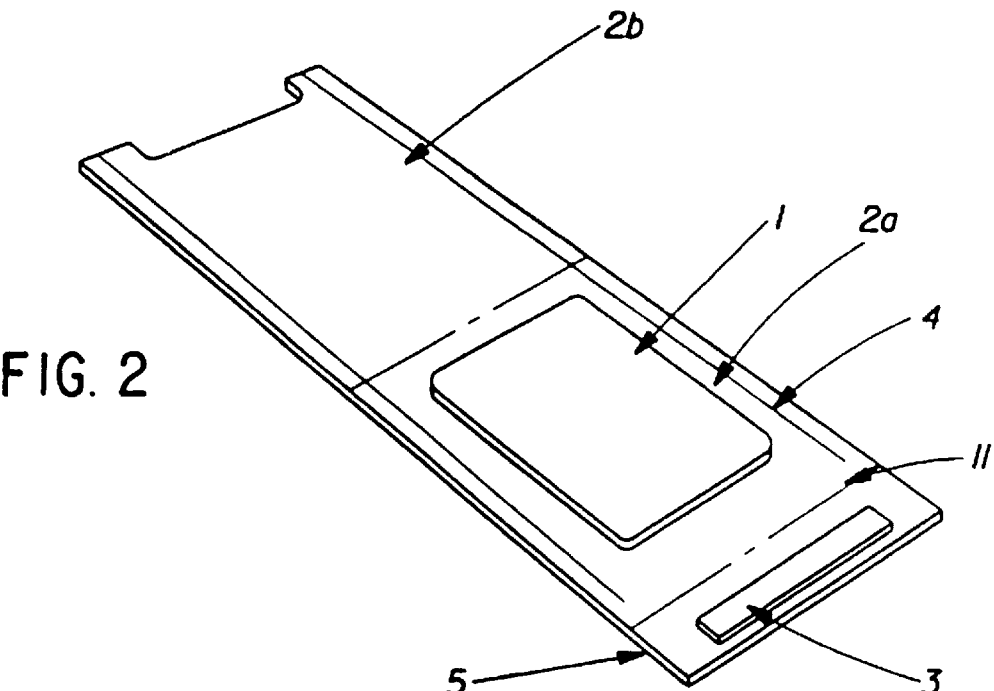
FIG. 2 is a perspective of the sheet loosely resting on a notched, vapor-venting containment bag which is in a pre-folded condition.

Substrates—The substrates herein are characterized by their oleophilic nature and by their ability to acquire a strong electrostatically positive charge when passed across or rubbed on the surface being cleaned. Such substrate materials had been available as the 9000 series KRYON™ Non-Wovens of J.P. Stevens Company, especially KRYON 9003. Such substrates are now available from Sommers Inc., 1410 Spruce Street, Stroudsburg, Pa. 18360, especially the chemically bonded non-wovens, available as Styles 235 and 265. SOMMERS Style 235 is a dry-layed, polyester fabric chemically bonded with an acrylic latex. The product weight (oz. per $yd^2$) is 0.9±10% (0.003 $g/cm^2$). Style 235 is available in a thickness of 0.009±0.001 inch (0.23±0.02 mm). SOMMERS Style 265 is likewise a dry-laid, polyester fabric chemically bonded with acrylic latex. It has a product weight (oz. per $yd^2$) of 1.5±10% (0.005 $g/cm^2$) and a thickness of 0.013±0.001 inch (0.33±0.2 mm). Such sheet-formed materials can be used herein as received from the manufacturer, or can be folded into multi-layer pads.

Apart from the commercially available SOMMERS (or counterpart KRYON) materials used herein, substrates useful herein can be made by adhering various commercial latex or acrylic latex suspensions on non-woven fabrics such as non-woven polyester available from Reemay. Whatever method is used to obtain the substrate, a simple test can be conducted to select substrates for use herein. One such test involves the use of a Faraday cage to measure the friction-induced build-up of electrical charge on the substrate. In this test (conducted at 74° F. (23° C.)/12% relative humidity) a 5 in.×6 in. (12.7×15.2 cm) sample of substrate is affixed to a wooden block (insulator) and hand-rubbed 20 strokes across DACRON™, nylon and Herculon™ carpeting. (The operator should wear rubber gloves to prevent charge bleed-off.) The substrate is promptly placed in the Faraday cage, and the charge is measured. Illustrative results are as follows.

| SUBSTRATE | NYLON | DACRON ™ | HERCULON ™ |
| --- | --- | --- | --- |
| SOMMERS 265 | +1.15 | +0.70 | +1.25 |
| SOMMERS 235 | +1.08 | +1.25 | +1.13 |
| KRYON 9003 | +1.09 | +0.66 | +1.28 |
| REEMAY (control)* | −0.08 | +0.07 | −0.60 |

*100% polyester; no binders or finishes.

Substrates useful in the present invention typically acquire a charge of at least about +0.5 volts on at least one, preferably all three, of the carpet samples in the above test. Preferably, the substrate acquires a charge of at least about 1.0 volts. If the substrate is desiccated, e.g., using heat, vacuum, water absorbents such as silica gel, etc., the acquired change can be increased by +0.5 to +1.0 volts. If the substrate is affixed to a heated block or carrier, the acquired charge can be as high as +3 volts. Different from the dryer-added sheets known in the art for fabric softening and anti-static benefits (e.g., BOUNCE™ sheets), the substrates herein do not contain cationic fabric softeners, since such softeners would tend to diminish the acquired positive charge.

Cleaning Method—A combination of two observed mechanisms would appear to be operating in this cleaning development. The first is an oleophilic attraction of the substrate herein for oils and gums on the surface being cleaned. Synthetic, non-woven fabrics made from polyester polyolefins (especially polypropylene) and nylon are sufficiently oleophilic to achieve this portion of the cleaning mechanism proposed herein. Polyester is preferred. The second is that the substrate herein can acquire a strong electrostatically positive charge when rubbed across the surface being cleaned. This strong positive charge relative to the cleaned surface causes particulate soil to be drawn to the substrate. As an overall proposition, and while not intending to be limited by theory, it is believed that the fiber used as the substrate should be a good electrical insulator and that the charge is picked up by the discontinuous treatment on the surface of the substrate, either in the binder or in finishing agents.

It is further to be noted that special packaging and operational methods can enhance the electrostatic effect of the substrates used herein. Desiccation during packaging and/or heating during use both can advantageously reduce humidity and moisture. It has been noted that high humidity and/or moisture can disadvantageously drain the charge build-up on the surface of the substrate. Thus, the surface being cleaned is preferably not wet. It is to be appreciated, however, that under usual conditions where humidity and moisture are dissipated, e.g., in a hot air clothes dryer, the substrates herein can be employed to advantage. When rendered sufficiently dry that they again can pick up the electrostatic charge, e.g., near the end of the drying cycle in an automatic clothes dryer, the substrates then regain their ability to function as a cleaning aid in the manner described herein.

Moreover, taking due consideration of the humidity/moisture limitations noted above, it has been determined that use of a suitable light solvent on the substrate can help soften gummy material present on the surface being cleaned, thereby further enhancing the cleaning effect. Materials such as monohydric alcohols and other non-aqueous solvents can be employed for this purpose. After evaporation of the light solvent, the electrostatic charge build-up attracts the loosened soils to the substrate.

The cleaning process herein is carried out simply, yet effectively, by rubbing the substrate across the surface to be cleaned. In one mode, this can be accomplished by simple hand-rubbing. Such a procedure is convenient for use when cleaning upholstered furniture, environmental surfaces such as furniture, tabletops, ornamental ware, and the like. This method can also be used for cleaning and removing detritus from hair and fur, such as on domestic and farm animals, and even human hair. This latter use is particularly helpful under circumstances where it is unhandy or difficult to employ conventional water-based shampoos, e.g., in a hospital environment, when traveling, and the like. In another mode, the substrate herein can be affixed to an apparatus, such as a mop, broom, vacuum sweeper, and the like, and rubbed across areas of floor carpeting, or the like.

In one variation, the substrate can be affixed to heated appliance (e.g., electrical heat) to soften gummy soils and to reduce the humidity of the substrate, thereby increasing the static charge. In still another mode, the articles are brought into intimate rubbing contact with garments which are tumbled together with the substrate in a conventional hot air clothes dryer. In yet another embodiment, the articles are affixed to a non-conductor, i.e., an electrically insulating implement, e.g., made of wood or plastic.

In still another embodiment, the articles herein can comprise the substrate in a sheet form which substantially encloses any hard, soft or semi-soft non-conductor material. For example, a latex block, sponge or the like can provide a semi-soft non-conductive "core" element whose outer surfaces are encased or otherwise enrobed in the sheet substrate. Alternatively, the core can comprise a soft material such as polyester or polypropylene or other fibrous batting. The core element provides additional bulk to such articles, thereby providing convenient gripping means for the user. In yet another mode, the sheet substrate can be fashioned into a pocket or pouch which removably encloses the non-conductor core. After use, the outer sheet with its layer of dirt and detritus can be removed from the core and discarded. The core can be re-used by placing it within a fresh pocket or pouch comprising the substrate sheet. In various other modes, the substrate can be fashioned into mitts, gloves, pads and the like to provide ease-of-use. In one embodiment, a mitt can be lined with a non-conductive material such as a polyethylene film which prevents the charge from bleeding off due to contact with moisture on the user's hand. The substrate can be provided in the form of rolls in the manner of disposable paper toweling, as individual sheets, and the like. These illustrations are given by way of explanation and not limitation of methods for using the substrates herein in a cleaning function. Whatever method or article is employed, the objective is to bring the substrate into close contact with the surface to be cleaned, said contact to be accompanied by a rubbing or other motion which causes the electrostatic charge to be developed on the surface of the substrate.

The size and shape of the substrate employed herein for cleaning purposes is dictated generally by matters of convenience in use and, of course, by the size of the article being cleaned and the degree of soiling. Conveniently sized substrates for use in cleaning hair, furniture, ornamental ware, tabletops, and the like, is about 12 inches×12 inches (30.5 cm×30.5 cm). The size of the substrate for use in an automatic clothes dryer can range from about 100 in$^2$ (645 cm$^2$) to about 500 in$^2$ (3226 cm$^2$).

The following examples illustrate various cleaning processes according to the present invention.

EXAMPLE I

A 15 cm×15 cm sheet of SOMMERS Style 235 is rubbed vigorously across a garment which is soiled with body soil and lint particles. The garment is satisfactorily cleaned.

EXAMPLE II

A 10 in.×10 in. (25.4 cm×25.4 cm) sheet of SOMMERS Style 265 is folded over twice to provide a pad weighing about 2.8 g. 1.0 Gram of substantially water-free (i.e., less than about 2%, by weight, of water) isopropanol is uniformly absorbed in the pad. The pad is packaged in a sealed foil pouch. In use, the pad is removed from the pouch and rubbed across the soiled surfaces of garments, upholstery, and the like to remove oily soil and detritus. In an optional mode, a light, substantially water-free perfume is added to the pad for aesthetic purposes.

EXAMPLE III

A sheet of SOMMERS Style 265 is rubbed on the fur of a domestic animal to remove soil. In an alternate mode, the sheet is lightly moistened (ca. 1 gram) with substantially water-free ethyl alcohol. The ethyl alcohol provides improved release of oily soils from the fur without interfering with the electrostatic attraction of the sheet for particulate soil.

EXAMPLE IV

A sheet (500 cm$^2$) of SOMMERS Style 235 or SOMMERS Style 265 fabric is placed together with damp fabrics in a conventional hot air clothes dryer. The dryer is operated in standard fashion whereby the tumbling action afforded to the fabrics and sheet causes them to come into close, rubbing contact. The dryer is operated until substantially all the moisture is removed from the fabric and the sheet, and tumbling is thereafter continued for an additional 1–10 minutes. The sheet helps remove particulate and oily soil present on the fabric surfaces.

In an alternate mode, hair, lint and other particulate detritus is removed from fabrics by placing dry fabrics in a conventional hot air clothes dryer and tumbling said fabrics with a sheet of SOMMERS Style 235 or SOMMERS Style 265 substrate for a period of about 1 minute to about 15 minutes.

EXAMPLE V

Electronic equipment, including phonograph records, compact discs, cathode ray tubes (e.g., TV screens and computer monitors) and the like can be cleaned by rubbing their surfaces with a sheet or pad of SOMMERS Style 235 or 265 substrate. In an alternate mode, the substrate can contain a small amount of volatile solvent such as ethanol or isopropanol to assist in the removal of oily material present on the surface of the electronic components.

Fabric Cleaning/Refreshment—While the foregoing examples illustrate the use of substrates herein in environments which, mainly, are substantially water-free, the following further illustrates the use of the compositions and processes embodied in the present invention in a home dry cleaning operation using fully formulated cleaning compositions which can contain water. In these processes, the sheet substrate is employed in combination with a cleaning composition and, preferably, a vented containment bag. In use, the moisture present in the cleaning composition first serves to assist in cleaning the fabrics and provides a dewrinkling and general fabric "refreshment" function, and is then vented from the bag by the heat of the laundry dryer. Once the moisture is removed, the sheet substrate herein can assume its electrostatic charge and attract and remove particulate soils. The following gives further details regarding the dry cleaning compositions which are suitable for use in such processes, as well as the vented cleaning bags which can be employed therein.

The dry cleaning process using a vapor-venting containment bag is conducted in a tumbling apparatus in the presence of heat. In a convenient mode a perforated or otherwise vapor-venting container bag with the article herein which comprises the carrier/cleaning composition and enveloping the soiled fabric is closed and placed in the drum of an automatic hot air clothes dryer. The drum is allowed to revolve, which imparts a tumbling action to the bag and agitation of its contents concurrently with the tumbling. By virtue of this agitation, the fabrics come in contact with the carrier containing the cleaning composition. The tumbling and heating are carried out for a period of at least about 10 minutes, typically from about 20 minutes to about 30 minutes. During this time, water and other vapors are vented from the bag. The process can be conducted for longer or shorter periods, depending on such factors as the degree and type of soiling of the fabrics, the nature of the soils, the nature of the fabrics, the fabric load, the amount of heat applied, and the like, according to the needs of the user.

The chemical compositions which are used to provide the cleaning function in the present in-dryer process comprise ingredients which are safe and effective for their intended use. Since the in-dryer cleaning/refreshment process herein does not involve an aqueous rinse step, the compositions employ ingredients which do not leave undesirable residues on fabrics when employed in the manner disclosed herein. While conventional laundry detergents are typically formulated to provide good cleaning on cotton and cotton/polyester blend fabrics, the cleaning compositions herein must be formulated to also safely and effectively clean and refresh fabrics such as wool, silk, rayon, rayon acetate, and the like.

In addition, the cleaning/refreshment compositions herein comprise ingredients which are specially selected and formulated to minimize dye removal from the fabrics being cleaned. In this regard, it is recognized that the solvents typically used in immersion dry cleaning processes can remove some portion of certain types of dyes from certain types of fabrics. However, such removal is tolerable in immersion processes since the dye is removed relatively uniformly across the surface of the fabric. In contrast, it has now been determined that high concentrations of certain types of cleaning ingredients at specific sites on fabric surfaces can result in unacceptable localized dye removal. The preferred cleaning compositions herein are formulated to minimize or avoid this problem.

The dye removal attributes of the present cleaning compositions can be compared with art-disclosed cleaners using photographic or photometric measurements, or by means of a simple, but effective, visual grading test. Numerical score units can be assigned to assist in visual grading and to allow for statistical treatment of the data, if desired. Thus, in one such test, a colored garment (typically, silk, which tends to be more susceptible to dye loss than most woolen or rayon fabrics) is treated by padding-on cleaner using an absorbent, white paper hand towel. Hand pressure is applied, and the amount of dye which is transferred onto the white towel is assessed visually.

In addition to the foregoing considerations, the cleaning/refreshment compositions used herein are preferably formulated such that they are not so adhesive in nature that they render the device unhandy or difficult to use. However, and while not intending to be limiting of the present invention, the preferred compositions disclosed herein afford a spot-cleaning process which is both effective and aesthetically pleasing when used with a device according to this invention.

Having due regard to the foregoing considerations, the following illustrates the ingredients used in the cleaning compositions herein, but is not intended to be limiting thereof.

(a) Solvent—The compositions may optionally comprise from about 2% to about 4%, typically from about 5% to about 25%, by weight, of organic cleaning solvent. If solvent is used, the objective is to provide at least about 0.4 g, preferably from about 0.5 g to about 2.5 g, of solvent per kg of fabrics being cleaned.

(b) Emulsifier—The compositions may optionally comprise sufficient emulsifier to provide a stable, homogeneous composition comprising components (a), (b) and (d). For the preferred emulsifiers disclosed hereinafter, levels as low as 0.05%, preferably 0.07% to about 0.20%, by weight, are quite satisfactory. If less efficient emulsifiers are used, levels up to about 2%, by weight, can be used, but may leave some noticeable residues on the fabrics.

(c) Water—The compositions may comprise about 60%, and can comprise from about 80% to about 95%, or even as high as about 99.75%, by weight, of water. For the in-dryer fabric process, the objective is to provide at least about 6 g of water per kg of fabrics being cleaned and refreshed.

(d) Optionals—The compositions herein may comprise various optional ingredients, including perfumes, conventional surfactants, and the like. If used, such optional ingredients will typically comprise from about 0.1% to about 10%, by weight, of the compositions, having due regard for residues on the cleaned fabrics.

It has now been determined that 1,2-octanediol ("OD") affords special advantages in the formulation of the cleaning compositions herein. From the standpoint of aesthetics, OD is a relatively innocuous and low odor material. Moreover, OD appears to volatilize from fabric surfaces without leaving visible residues. This is especially important in a dry cleaning process of the present type which is conducted without a rinse step. From the performance standpoint, OD appears to function both as a solvent for greasy/oily stains and as what might be termed a "pseudo-surfactant" for particulate soils and water-soluble stains. Whatever the physical-chemical reason, OD has now been found to be a superior wetting agent with respect to both cleaning and ease-of-use in the present context of home-use cleaning compositions and processes. If used, OD will comprise at least about 0.05%, typically from about 0.1% to about 1.5%, by weight of the cleaning compositions herein.

A preferred solvent herein is butoxy propoxy propanol (BPP) which is available in commercial quantities as a mixture of isomers in about equal amounts. The isomers, and mixtures thereof, are useful herein. The isomer structures are as follows:

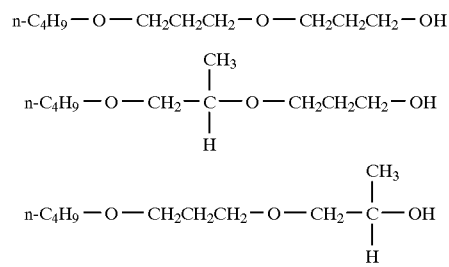

BPP is outstanding for cleaning, and is so effective that it allows the amount of the relatively expensive 1,2-octanediol to be minimized. Moreover, it allows for the formulation of effective cleaning compositions herein without the use of conventional surfactants. Importantly, the odor of BPP is of a degree and character that it can be relatively easily masked by conventional perfume ingredients. While BPP is not completely miscible with water and, hence, could negatively impact processing of the cleaning compositions herein, that potential problem has been successfully overcome by means of the PEMULEN-type polyacrylate emulsifiers, as disclosed hereinafter.

The BPP solvent used herein is preferably a mixture of the aforesaid isomers. In a preferred mode, the cleaning compositions comprise a mixture of the 1,2-octanediol and BPP, at a weight ratio of OD:BPP in the range of from about 1:250 to about 2:1, preferably from about 1:200 to about 1:5.

A highly preferred emulsifier herein is commercially available under the trademark PEMULEN, The B.F. Goodrich Company, and is described in U.S. Pat. Nos. 4,758,641 and 5,004,557, incorporated herein by reference. PEMULEN polymeric emulsifiers are high molecular weight polyacrylic acid polymers. The structure of PEMULEN includes a small portion that is oil-loving (lipophilic) and a large water-loving (hydrophilic) portion. The structure allows PEMULEN to function as a primary oil-in-water emulsifier. The lipophilic portion adsorbs at the oil-water interface, and the hydrophilic portion swells in the water forming a network around the oil droplets to provide emulsion stability. An important advantage for the use of such polyacrylate emulsifiers herein is that cleaning compositions can be prepared which contain solvents or levels of solvents that are otherwise not soluble or readily miscible with water. A further advantage is that effective emulsification can be accomplished using PEMULEN-type emulsifier at extremely low usage levels (0.05–0.2%), thereby minimizing the level of any residue left on fabrics following product usage. For comparison, typically about 3–7% of conventional anionic or nonionic surfactants are required to stabilize oil-in-water emulsions, which increases the likelihood that a residue will be left on the fabrics. Another advantage is that emulsification (processing) can be accomplished effectively at room temperature.

While the cleaning compositions herein function quite well with only the 1,2-octanediol, BPP, Pemulen and water, they may also optionally contain detersive surfactants to further enhance their cleaning performance. While a wide variety of detersive surfactants such as the $C_{12}$–$C_{16}$ alkyl sulfates and alkylbenzene sulfonates, the $C_{12}$–$C_{16}$ ethoxylated (EO 0.5–10 avg.) alcohols, the $C_{12}$–$C_{14}$ N-methyl glucamides, and the like can be used herein, it is highly preferred to use surfactants which provide high grease/oil removal. Included among such preferred surfactants are the $C_{12}$–$C_{16}$ alkyl ethoxy sulfates (AES), especially in their magnesium salt form, and the $C_{12}$–$C_{16}$ dimethyl amine oxides. Especially preferred mixtures comprise $MgAE_1S$/$C_{12}$ dimethyl amine oxide, at a weight ratio of about 10:1, and $MgAE_1S$/$C_{12}$ dimethyl amine oxide at a 2:1 weight ratio. If used, such surfactants will typically comprise from about 0.05% to about 2.5%, by weight, of the cleaning compositions herein.

In addition to the preferred solvents and emulsifiers disclosed above, the cleaning compositions herein may comprise various optional ingredients, such as perfumes, preservatives, co-solvents, brighteners, salts for viscosity control, pH adjusters or buffers, anti-static agents such as VERSAFLEX 157 or VERSAFLEX 2004 from National Starch and Chemical Company, softeners, colorants, mothproofing agents, insect repellents, and the like. Enzymes such as proteases, amylases, lipases and mixtures thereof can also be used at levels from about 0.0001% to about 1% of the compositions. The following illustrates preferred ranges for cleaning compositions for use herein, but is not intended to be limiting thereof

| Ingredient | % (wt.) Formula Range |
|---|---|
| BPP* | 5–25% |
| 1,2-Octanediol | 0.1–7% |
| PEMULEN** | 0.05–0.20% |
| Neodol 23–6.5*** | 0.1–2.5% |
| Perfume | 0.01–1.5% |
| Water | Balance |
| pH range from about 6 to about 8. | |

*Other solvents or co-solvents which can be used herein include various glycol ethers, including materials marketed under trademarks such as Carbitol, methyl Carbitol, butyl Carbitol, propyl Carbitol, and hexyl Cellosolve, and especially methoxy propoxy propanol (MPP), ethoxy propoxy propanol (EPP), propoxy propoxy propanol (PPP), and all isomers and mixtures, respectively, of MPP, EPP, and PPP, and the like, and mixtures thereof. Indeed, although somewhat less preferred, the MPP, EPP and PPP, respectively, can replace the BPP solvent in the foregoing cleaning compositions. The levels of these solvents, and their ratios with 1,2-octanediol, are the same as with the preferred BPP solvent. If desired, and having due regard for safety and odor for in-home use, various conventional chlorinated and hydrocarbon dry cleaning solvents may also be used. Included among these are 1,2-dichloroethane, trichloroethylene, isoparaffins, and mixtures thereof.
**As disclosed in U. S. Pat. 4,758,641 and 5,004,557, such polyacrylates include homopolymers which may be crosslinked to varying degrees, as well as non-crosslinked. Preferred herein are homopolymers having a molecular weight in the range of from about 100,000 to about 10,000,000, preferably 200,000 to 5,000,000.

| Ingredient | % (wt.) Formula Range |
|---|---|

***$C_{12–13}$ alcohol average ethoxylate (EO) 6.5; trademark Shell removal from fabrics as disclosed above is as follows.

A dry cleaning composition with reduced tendency to cause dye "bleeding" or removal from fabrics as disclosed above is as follows.

| INGREDIENT | PERCENT (wt.) | (RANGE) |
|---|---|---|
| Butoxypropoxy propanol (BPP) | 7.000 | 4.0–25.0% |
| NEODOL 23-6.5* | 0.750 | 0.05–2.5% |
| 1,2-Octanediol | 0.500 | 0.1–10.0% |
| Perfume | 0.750 | 0.1–2.0% |
| Pemulen TR-1 | 0.125 | 0.05–0.2% |
| Potassium Hydroxide (KOH) | 0.060 | 0.024–0.10 |
| Potassium Chloride | 0.075 | 0.02–0.20 |
| Water (distilled or deionized) | 90.740 | 60.0–95.0% |
| Target pH = 7.0 | | |

*Shell; $C_{12}$–$C_{13}$ alcohol, ethoxylated with average EO of 6.5.

Another in-dryer cleaning and fabric refreshment composition useful herein is as follows.

EXAMPLE VI

High water content ("Sweet Water"), low residue cleaning/refreshment compositions for use in the in-dryer fabric cleaning/refreshment processes herein are as follows. The compositions are used in the manner disclosed hereinabove to clean and refresh fabrics.

| Components | Percent | Range (%) | Function |
|---|---|---|---|
| Water De-ionized | 98.8997 | 97–99.9 | Vapor Phase Cleaning |
| TWEEN 20 | 0.50 | 0.5–1.0 | Wetting Agent |
| Perfume | 0.50 | 0.1–1.50 | Scent, Aesthetics |
| KATHON CG* | 0.0003 | 0.0001–0.0030 | Anti-bacterial |
| Sodium Benzoate* | 0.10 | 0.05–1.0 | Anti-fungal |

*Optional preservative ingredients.

20–30 grams, preferably about 23 grams, of the "Sweet Water" composition are absorbed into a SOMMERS 235 or 265 (28 cm×38 cm) carrier sheet (the sheet is preferably not "dripping" wet) which is of a size which provides sufficient surface area that effective contact between the surface of the carrier sheet and the surface of the fabrics being cleaned and refreshed is achieved. The sheet is used in the manner described hereinafter to clean and refresh fabrics in a hot air clothes dryer.

Besides the optional nonionic surfactants in the cleaning compositions herein, which are preferably $C_8$–$C_{18}$ ethoxylated (E01-15) alcohols or the corresponding ethoxylated alkyl phenols, the compositions can contain enzymes to further enhance cleaning performance. Lipases, amylases and protease enzymes, or mixtures thereof, can be used. If used, such enzymes will typically comprise from about 0.001% to about 5%, preferably from about 0.01% to about 1%, by weight, of the composition. Commercial detersive enzymes such as LIPOLASE, ESPERASE, ALCALASE, SAVINASE and TERMAMYL (all ex. NOVO) and MAXATASE and RAPIDASE (ex. International Bio-Synthesis, Inc.) can be used. The compositions herein can optionally be stabilized for storage using conventional preservatives such as KATHON® at a level of 0.0001%–1%, by weight.

The garments or other fabrics to be cleaned/refreshed are loaded into a vapor-venting containment bag as shown in the Figures together with a sheet according to this Example VI. The bag is closed and tumbled in a conventional hot air clothes dryer for 30–60 minutes at temperatures above about 50° C., typically 50–85° C. but ranging in some dryers as high as 200° C., and above, depending on dryer design, dryer vent design and like factors. In general, the "high" heat setting of the dryer is used. As shown in the Figures, the preferred bag used in this step is provided with a vapor-venting closure which provides one or more gaps through which vapors are released from the bag, in-use. Alternatively, the bag can be provided with a series of holes or other fenestrations which provide vapor venting. However, such venting is not as effective as the vapor-venting closure shown in the Figures.

In one embodiment, the vapor-venting containment bag comprises an open end, a closed end and flexible side walls having inner and outer surfaces, the open end of said bag having a section of one side wall extending beyond said open end to provide a flexible flap, said flap having first fastening device affixed thereto, said flap being foldable to extend over a portion of the outside surface of the opposing side wall, said flap being affixable to the outer surface of the opposing wall of the bag by engaging said first fastening device on the inside face of the flap with a second fastening device present on the outside face of said opposing side wall, said first and second fastening devices, when thus engaged, forming a fastener, thereby providing a closure for the open end of the bag. Said first and second fastening devices are disposed so as, when engaged, to provide vapor-venting along said closure, especially at the lateral edges of the closure. The bag herein is most preferably formed from film which is heat resistant up to at least about 204° C.–260° C. Nylon is a preferred film material for forming the bag. In another embodiment, the edge of one wall of the bag is notched along a substantial portion of its width to facilitate and optimize vapor venting.

In an alternate mode, the flap can be folded to provide the closure, tucked inside the opposing side wall, and secured there by a fastener. In this mode, vapors are vented along the closure and especially at the lateral edges of the closure. In yet another mode, the side walls are of the same size and no flap is provided. Fastening devices placed intermittently along portions of the inner surfaces of the side walls are engaged when the lips of the side walls are pressed together to provide closure. One or more vapor-venting gaps are formed in those regions of the closure where no fastening device is present.

While the fastening devices herein can comprise chemical adhesives, the bag is preferably designed for multiple uses. Accordingly, reusable mechanical fasteners are preferred for use herein. Any reusable mechanical fastener or fastening means can be used, as long as the elements of the fastener can be arranged so that, when the bag is closed and the fastener is engaged, a vapor-venting closure is provided. Non-limiting examples include: bags wherein said first and second fastening devices, together, comprise a hook and loop (VELCRO®-type) fastener; hook fasteners such as described in U.S. Pat. No. 5,058,247 to Thomas & Blaney issued Oct. 22, 1991, bags wherein said first and second fastening devices, together, comprise a hook and string type fastener; bags wherein said first and second fastener devices, together, comprise an adhesive fastener; bags wherein said first and second fastening devices, together, comprise a toggle-type fastener; bags wherein said first and second fastening devices, together, form a snap-type fastener; as well as hook and eye fasteners, ZIP LOK®-style fasteners, zipper-type fasteners, and the like, so long as the fasteners are situated so that vapor venting is achieved. Other fasteners can be employed, so long as the vapor-venting is maintained when the bag is closed, and the fastener is sufficiently robust that the flap does not open as the bag and its contents are being tumbled in the clothes dryer. The fastening devices can be situated that the multiple vapor-venting gaps are formed along the closure, or at the lateral edges, or so that the gap is offset to one end of the closure. In yet another embodiment, both ends of the bag are provided with a vapor venting closure.

Figure 3:
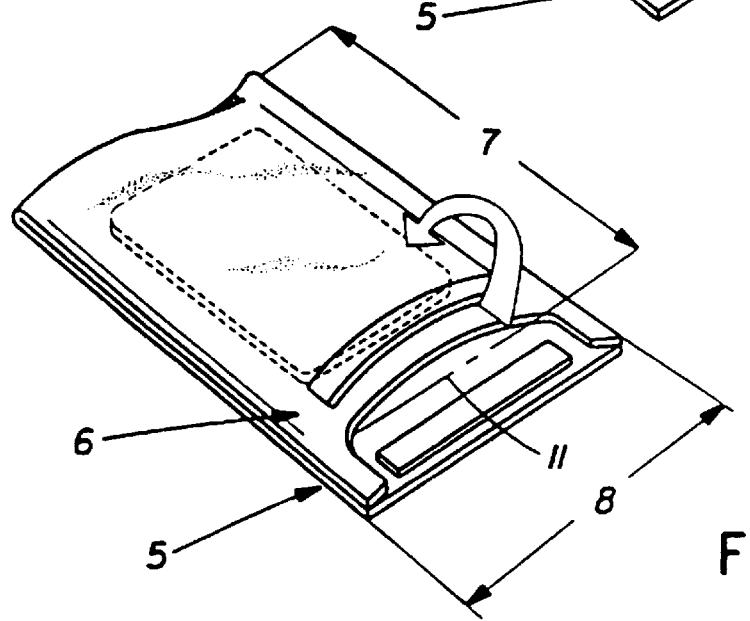
FIG. 3 is a perspective of the sheet within the bag which is ready to be treated in a hot air clothes dryer.

FIG. 3 shows the overall dimensions of a notched bag: i.e., length (7) to fold line 27⅝ inches (70.2 cm); width (8) of bag 26 inches (66 cm), with a flap to the base of the fold line (11) of 2⅜ inches (6 cm). In the Tests reported hereinafter, this bag is referred to by its open dimensions as "26 in.×30 in." (66.04 cm×76.20 cm).

Figure 4:
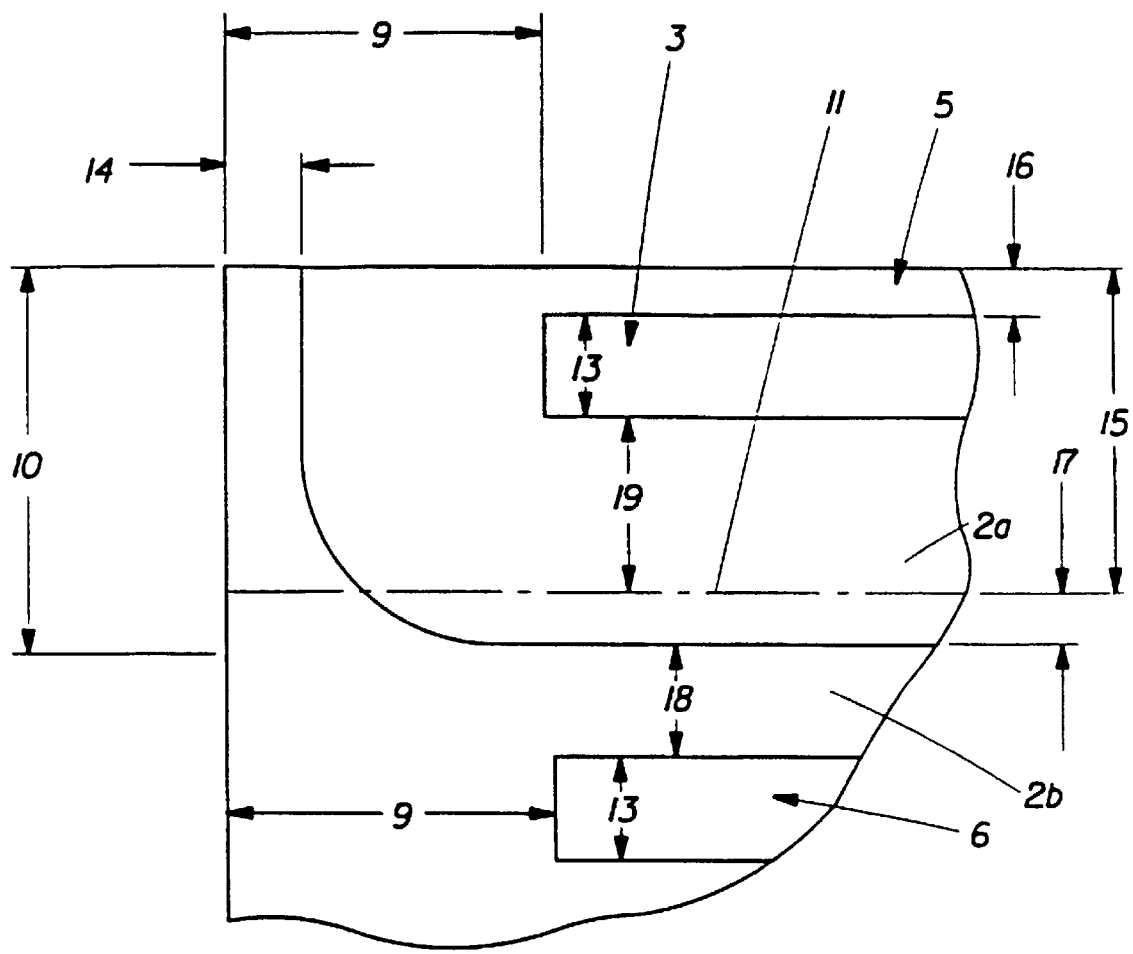
FIG. 4 is a partial view of the notched wall of the bag and its disposition relative to the closure flap.

FIG. 4 gives additional details of the positioning of the various elements of the notched bag. In this embodiment, all dimensions are the same for both the left hand and right hand sides of the bag. The dimensions herein are for an opened bag which is about 30 inches (76.2 cm) in overall length (including the flap) and about 26 inches (66 cm) wide. The distance (9) from the lateral edge of the bag to the outermost edge of the fastening device (3) located on the inside of the flap (5) is about 2 inches (5 cm). In this embodiment, the fastening device (3) on the inside of wall (2a) comprises the loop portion of a VELCRO®-type strip whose width (13) is about 0.75 inches (1.9 cm) and whose total length is about 22 inches (55.9 cm). Fastening device (6) is similarly situated on the outside of wall 2(b) and comprises the hook portion of a ¾ inch (1.9 cm) VELCRO®-type strip. Distance (9) can be decreased or increased to decrease or increase venting at the edges of the flap when the bag is closed and the fastener is engaged. The distance (10) between the uppermost edge of the flap and the base of the notch is about 2⅞ inches (7.3 cm). The distance (14) between the lateral edge of the bag and the lateral edge of the notch is about 0.25 inches (0.64 cm). The distance (15) between the uppermost edge of the flap and the fold (11) is about 2⅜ inches (6 cm). The distance (16) between the uppermost edge of the flap and the leading edge of the VELCRO®-type strip (3) affixed to the flap is about ⅜ inches (0.95 cm). The distance (17) between fold (11) and the lowermost edge of the notch is about ½ inch (1.27 cm). This distance also can be varied to decrease or increase vapor venting. A range of 0.25–1.5 inches (0.64–3.81 cm) is typical. The distance (18) between the uppermost edge of the VELCRO®-type strip (6) and the bottom edge of the notch is about ¾ inches (1.9 cm). The distance (19) between the bottommost edge of the VELCRO®-type strip (3) and the fold (11) is about 1¼ inches (3.17 cm).

Figure 5:
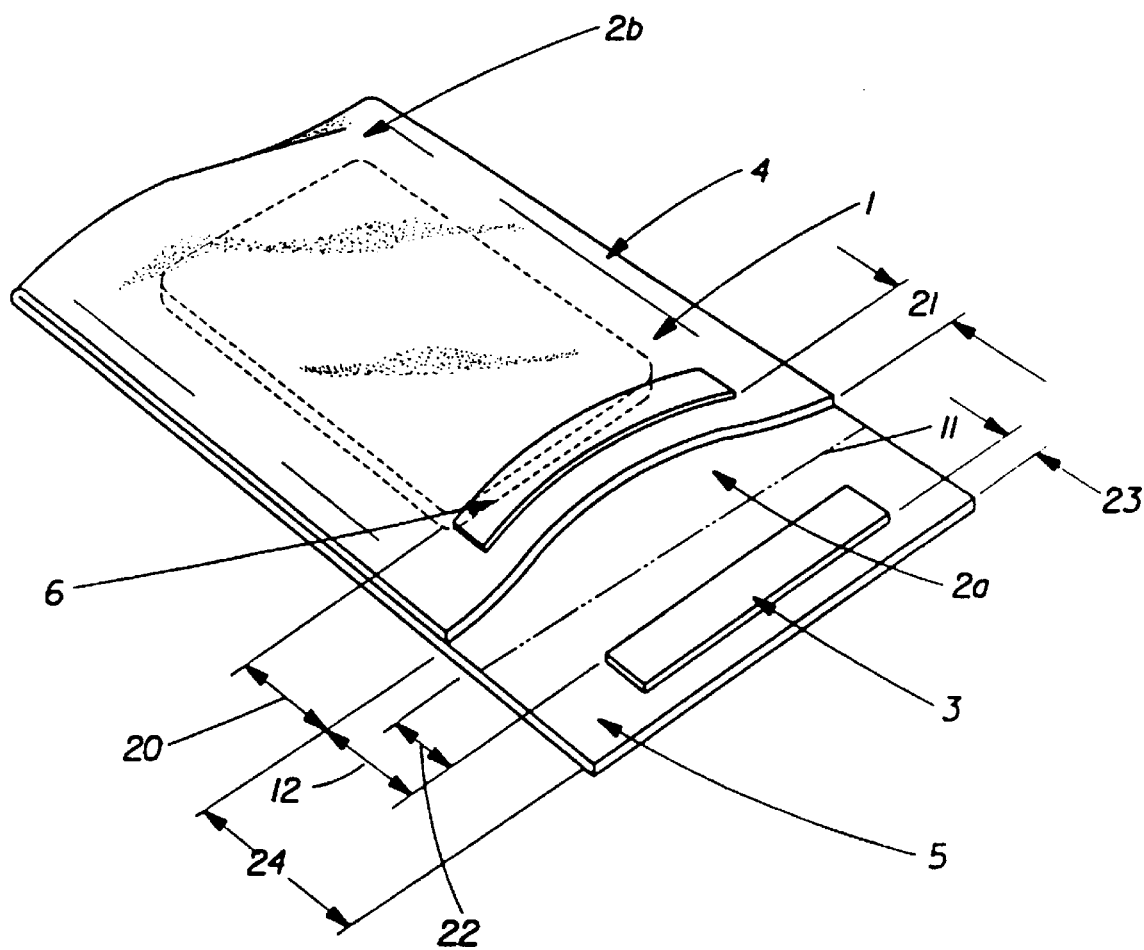
FIG. 5 is a perspective of an un-notched vapor-venting bag containing a sheet which is ready for use in the present process.

FIG. 5 gives additional details of the dimensions of an un-notched envelope bag of the foregoing overall size comprising sidewalls (2a) and (2b). Again, each VELCRO®-type strip (3) and (6) is about ¾ inches (1.9 cm) in width and about 22 inches (55.9 cm) in length. Each strip is positioned so as to be inboard from each of the lateral edges of the finished bag wall and flap by about 2 inches (5 cm). The distance (12) between the leading edge of the sidewall (2b) to the base edge of the fastener strip (3) on the flap portion of the bag is about 2½ inches (6.35 cm). The distance (20) between the base edge of the fastener strip (6) to the leading edge of the sidewall (2b) is about 2.25 inches (5.7 cm). The distance (21) between the leading edge of the fastener strip (6) to the leading edge of the sidewall is about 1⅜ inches (3.5 cm). The distance (22) between fold (11) and the base edge of the fastener strip (3) is about 2 inches (5 cm). The distance (23) between the leading edge of fastener strip (3) and the uppermost edge of the flap which is an extension of sidewall (2a) is about 0.25 inches (0.64 cm). Distance (24) is about 3⅝ inches (9.2 cm). As in the foregoing notched bag, the positioning and length of the fasteners can be adjusted to decrease or increase venting.

The construction of the preferred, heat-resistant vapor-venting bag used herein to contain the fabrics in a hot air laundry dryer or similar device preferably employs thermal resistant films to provide the needed temperature resistance to internal self-sealing and external surface deformation sometimes caused by overheated clothes dryers. In addition, the bags are resistant to the chemical agents used in the cleaning or refreshment compositions herein. By proper selection of bag material, unacceptable results such as bag melting, melted holes in bags, and sealing of bag wall-to-wall are avoided. In a preferred mode, the fastener is also constructed of a thermal resistant material. As shown in FIGS. 3 and 5, in one embodiment, 1 to 3 mil (0.025–0.076 mm) heat-resistant Nylon-6 film is folded and sealed into a containment bag. Sealing can be done using standard impulse heating equipment. In an alternate mode, a sheet of nylon is simply folded in half and sealed along two of its edges. In yet another mode, bags can be made by air blowing operations. The method of assembling the bags can be varied, depending on the equipment available to the manufacturer and is not critical to the practice of the invention.

The dimensions of the containment bag can vary, depending on the intended end-use. For example, a relatively smaller bag can be provided which is sufficient to contain one or two blouses. Alternatively, a larger bag suitable for handling a man's athletic garment can be provided. Typically, the bags herein will have an internal volume of from about 10,000 cm$^3$ to about 25,000 cm$^3$. Bags in this size range are sufficient to accommodate a reasonable load of fabrics (e.g., 0.2–5 kg) without being so large as to block dryer vents in most U.S.-style home dryers. Somewhat smaller bags may be used in relatively smaller European and Japanese dryers.

The bag herein is preferably flexible, yet is preferably durable enough to withstand multiple uses. The bag also preferably has sufficient stiffness that it can billow, in-use, thereby allowing its contents to tumble freely within the bag during use. Typically, such bags are prepared from 0.025 mm to 0.076 mm (1–3 mil) thickness polymer sheets. If more rigidity in the bag is desired, somewhat thicker sheets can be used.

In addition to thermally stable "nylon-only" bags, the containment bags herein can also be prepared using sheets of co-extruded nylon and/or polyester or nylon and/or polyester outer and/or inner layers surrounding a less thermally suitable inner core such as polypropylene. In an alternate mode, a bag is constructed using a nonwoven outer "shell" comprising a heat-resistant material such as nylon or polyethylene terephthalate and an inner sheet of a polymer which provides a vapor barrier. The non-woven outer shell protects the bag from melting and provides an improved tactile impression to the user. Whatever the construction, the objective is to protect the bag's integrity under conditions of thermal stress at temperatures up to at least about 400–500° F. (204° C. to 260° C.). Under circumstances where excessive heating is not of concern, the bag can be made of polyester, polypropylene or any convenient polymer material.

The dimensions of the containment bag can also vary, depending on the intended end-use. For example, a bag can be provided which is sufficient to contain one or two silk blouses. Alternatively, a bag suitable for handling a man's suit can be provided. As noted, the bags herein will typically have an internal volume of from about 10,000 cm$^3$ to about 25,000 cm$^3$. Bags in this size range are sufficient to accommodate a reasonable load of fabrics (e.g., 0.5–5 kg) without being so large as to block dryer vents.

In a preferred embodiment, 0.025 mm to 0.075 mm nylon film is sealed into a 26 inch (66 cm)×30 in. (76 cm) bag. Sealing is preferably done using standard impulse heating equipment. In an alternate mode, a sheet of nylon is simply folded in half and sealed along two of its edges. In yet another mode, bags can be made by air blowing operations.

As noted, in addition to bags with the vapor-venting closure, the walls of bags which are made from polymer sheet stock can be provided with slits, holes (preferred) or the like to provide means for the venting to occur. This can be simply, yet effectively, achieved by punching holes in the walls of the bag using any convenient instrument. In a typical mode, 5–20 pairs of ¼ inch (0.6 cm)–1 inch (2.54 cm) holes are uniformly punched in the walls of a substantially rectangular bag having a total volume of about 25,000 cm$^3$. This provides adequate venting in the process herein. In another mode, a series of longitudinal slits are cut in the walls of the bag.

EXAMPLE VII

The foregoing Examples illustrate the use of a commercially available substrate herein. This Example illustrates the preparation of a substrate sheet for use herein. In this process, the acrylic latex "bonding" or "coating" is applied by means of a spray-on rather than a dip coating, since it is preferred that the latex be present on the sheet in discrete, discontinuous spots rather than as a continuous layer of coating. In one mode of manufacture, TEC brand acrylic latex emulsion #869 (TEC Incorporated, an H.B. Fuller company) is sprayed with a hand pump sprayer onto both sides of commercial Reemay polyester non-woven fabric of the type described above, typically, but not limited to, fabric having a weight (oz. per yd$^2$) in the 0.8–1.6 (0.0026 g/cm$^2$–0.0053 g/cm$^2$) range. After drying overnight at ambient temperature, it is determined that about 9.0 wt. %, based on the original fabric weight, is present as dried residual acrylic latex. Samples prepared in this manner test as +0.07 volts untreated (control) vs. +0.67 volts treated with the acrylic latex. As a range, acrylic latex-loaded samples prepared in this manner typically comprise about 4% to about 12% added acrylic latex, by weight. This results in about 0.5 to about 1.2 added positive volts in the electrostatic test described above.

Sheets of the foregoing type with the acrylic binder, preferably as a discontinuous coating, are used in the manner of any of the foregoing Examples by placing them in contact with and passing them across a soiled surface, thereby cleaning all manner of surfaces, including fabrics.

What is claimed is:

1. An article for cleaning surfaces, comprising:
   (a) a substrate, having an oleophilic nature and an ability to acquire a strong electrostatically positive charge of at least 0.5 Volts when passed across the surface being cleaned; and
   (b) said substrate is a dry-laid polyester bonded with acrylic latex and said substrate releasably contains an auxiliary cleaning composition comprising a monohydric alcohol.

2. An article according to claim 1 wherein said substrate is fibrous.

3. An article according to claim 1 wherein the auxiliary cleaning composition comprises a monohydric alcohol which is a member selected from the group consisting of ethanol, isopropanol, and mixtures thereof.

4. An article according to claim 1 wherein the auxiliary cleaning composition comprises a member selected from the group consisting of methoxy-, ethoxy-, propoxy- and butoxy-propoxypropanol.

5. An article according to claim 1 wherein the auxiliary cleaning composition further comprises 1,2-octanediol.

6. An article according to claim 1 wherein the auxiliary cleaning composition further comprises a nonionic surfactant.

7. An article according to claim 1 wherein the auxiliary cleaning composition comprises a mixture of butoxy-propoxypropanol and 1,2-octanediol.

8. An article according to claim 1 wherein the cleaning composition comprises a mixture of butoxy-propoxypropanol, 1,2-octanediol and an ethoxylated alcohol or alkyl phenol.

9. A process for cleaning surfaces, comprising contacting said surfaces with the article for cleaning surfaces according to claim 1.

10. A process according to claim 9 wherein the substrate is mounted on or encases an electrically non-conductive implement or core material.

11. A process according to claim 9 wherein the auxiliary cleaning composition is non-aqueous.

12. A process according to claim 11 wherein the auxiliary cleaning composition comprises a monohydric alcohol which is a member selected from the group consisting of ethanol, isopropanol, and mixtures thereof.

13. A process according to claim 11 wherein the auxiliary cleaning composition comprises a member selected from the group consisting of methoxy-, ethoxy-, propoxy- and butoxy-propoxypropanol.

14. A process according to claim 11 wherein the auxiliary cleaning composition further comprises 1,2-octanediol.

15. A process according to claim 11 wherein the auxiliary cleaning composition further comprises a nonionic surfactant.

16. A process according to claim 11 wherein the auxiliary cleaning composition comprises a mixture of butoxy-propoxypropanol and 1,2-octanediol.

17. A process according to claim 11 wherein the cleaning composition comprises a mixture of butoxy-propoxypropanol, 1,2-octanediol and an ethoxylated alcohol or alkyl phenol.

18. A process for cleaning fabrics in a conventional automatic clothes dryer, comprising the steps of placing soiled fabrics together with the article for cleaning surfaces according to claim 1 in the drum of the clothes dryer, and operating the dryer under conventional usage conditions involving rotation of the dryer drum and the introduction of hot air into the drum.

19. A process according to claim 18 wherein the cleaning composition comprises a member selected from the group consisting of methoxy-, ethoxy-, propoxy- and butoxy-propoxypropanol.

20. A process according to claim 18 wherein the cleaning composition further comprises 1,2-octanediol.

21. A process according to claim 18 wherein the cleaning composition further comprises a mixture of water and a member selected from the group consisting of nonionic surfactants, butoxy-propoxypropanol, 1,2-octanediol, and mixtures thereof.

22. A process according to claim 18 wherein the auxiliary composition further comprises water and a nonionic surfactant.

23. A process according to claim 18 wherein the soiled fabrics and the article are contained within a vapor-venting bag.

24. An article of manufacture comprising the article for cleaning surfaces according to claim 1 said substrate being affixed to or enrobing or otherwise encasing an electrically non-conductive core element.

25. An article according to claim 24 which can be heated.

26. An article according to claim 24 wherein the core element comprises a member selected from the group consisting of fibrous batting and sponge.

* * * * *